(12) United States Patent
Lee

(10) Patent No.: US 6,787,773 B1
(45) Date of Patent: Sep. 7, 2004

(54) FILM THICKNESS MEASUREMENT USING ELECTRON-BEAM INDUCED X-RAY MICROANALYSIS

(75) Inventor: Shing M. Lee, Fremont, CA (US)

(73) Assignee: KLA-Tencor Corporation, San Jose, CA (US)

(*) Notice: Subject to any disclaimer, the term of this patent is extended or adjusted under 35 U.S.C. 154(b) by 0 days.

(21) Appl. No.: 09/695,726

(22) Filed: Oct. 23, 2000

Related U.S. Application Data

(60) Provisional application No. 60/210,337, filed on Jun. 7, 2000.

(51) Int. Cl.[7] .................................................. G21K 7/00
(52) U.S. Cl. .................... 250/311; 250/310; 250/339.01
(58) Field of Search ................................ 250/310, 311, 250/307, 288; 378/46, 45, 50, 49, 84, 83, 82

(56) References Cited

U.S. PATENT DOCUMENTS

| | | | |
|---|---|---|---|
| 4,162,528 A | * | 7/1979 | Maldonado et al. ........ 702/172 |
| 4,472,825 A | | 9/1984 | Jenkins |
| 4,476,386 A | | 10/1984 | Reid et al. |
| 4,534,049 A | | 8/1985 | Koga |
| 4,675,889 A | | 6/1987 | Wood et al. |
| 4,777,364 A | | 10/1988 | Sartore |
| H589 H | * | 2/1989 | Sartore ....................... 250/307 |
| 4,885,465 A | | 12/1989 | Nagatsuka et al. |
| 4,959,848 A | | 9/1990 | Parobek |
| 4,962,516 A | * | 10/1990 | Soezima ..................... 250/307 |
| 5,055,679 A | | 10/1991 | Ninomiya et al. |
| 5,060,247 A | | 10/1991 | Watanabe |

(List continued on next page.)

FOREIGN PATENT DOCUMENTS

JP         6-267485         9/1994

OTHER PUBLICATIONS

J.L. Pouchou and F. Pichoir, "Electron Probe X–Ray Microanalysis Applied To Thin Surface Films and Stratified Specimens", Scanning Microscopy, Supplement 7., (1993), pp. 167–189.

(List continued on next page.)

*Primary Examiner*—John R. Lee
*Assistant Examiner*—Kalimah Fernandez
(74) *Attorney, Agent, or Firm*—Beyer Weaver & Thomas, LLP

(57) ABSTRACT

An X-ray micoanalysis test system comprising a beam generator which induces X-rays to emanate from a semiconductor device containing film stacks. The charged particle beam will penetrate at least two layers of a film stack on a semiconductor device so that these layers may be tested. The X-rays will be detected using multiple X-ray detectors that detect X-ray photons having a specific energy level. The X-rays will then be used to analyze the characteristics of the semiconductor device. Each of the multiple X-ray detectors may be wavelength dispersive system (WDS) detectors. The present invention also provides a method for measuring film stack characteristics on a semiconductor device. The method for measuring includes directing an electron beam towards the semiconductor device so that the electron beam penetrates at least a conductive film layer and a liner layer, detecting the X-rays which are caused to emanate from the device with multiple X-ray detectors that detect X-ray photons having a specific energy level. The present invention also provides a method and a computer-readable medium which determines a film stack's properties using the data collected with the test system of the present invention. The method and computer-readable medium includes selecting a set of values which estimate the film stack characteristics, using the estimated values to generate predicted data by solving equations which model the film stack, and selecting a new set of estimated film stack characteristic values when the difference between the predicted data and the raw data is larger than a certain margin of error.

28 Claims, 9 Drawing Sheets

U.S. PATENT DOCUMENTS

| | | | |
|---|---|---|---|
| 5,065,020 A | | 11/1991 | Kanda |
| 5,210,414 A | * | 5/1993 | Wallace et al. ............. 250/307 |
| 5,299,252 A | | 3/1994 | Takahashi |
| 5,350,921 A | | 9/1994 | Aoyama et al. |
| 5,485,499 A | | 1/1996 | Pew et al. |
| 5,530,732 A | | 6/1996 | Takemi |
| 5,594,246 A | * | 1/1997 | Sudo et al. ................. 250/310 |
| 5,596,195 A | | 1/1997 | Obori et al. |
| 5,656,812 A | | 8/1997 | Takahashi |
| 5,657,363 A | | 8/1997 | Hossain et al. |
| 5,703,361 A | * | 12/1997 | Sartore ....................... 250/307 |
| 5,705,878 A | | 1/1998 | Lewis et al. ................ 310/328 |
| 5,754,620 A | | 5/1998 | Hossain et al. |
| 5,777,336 A | | 7/1998 | Silver et al. |
| 5,866,903 A | | 2/1999 | Morita et al. |
| 5,877,498 A | * | 3/1999 | Sugimoto et al. ........... 250/310 |
| 5,892,809 A | | 4/1999 | Wittry |
| 5,926,522 A | * | 7/1999 | McCarthy et al. .......... 378/145 |
| 6,351,516 B1 | * | 2/2002 | Mazor et al. ................. 378/44 |
| 6,353,222 B1 | | 3/2002 | Dotan ......................... 250/310 |
| 6,385,281 B1 | * | 5/2002 | Ozawa et al. ................. 378/45 |

OTHER PUBLICATIONS

"High–Resolution X–ray Microanalysis for Low Voltage Applications", Noran Instruments, (1997), 5 pages.

M. Stavrev[a], D. Fischer[a], C. Wenzel[a], and T. Heiser[b], "Study of Ta(N,O) diffusion barrier stability: analytical and electrical characterization of low level Cu contamination in Si", Microelectronic Engineering, 37/38 (1997) pp. 245–251.

JeanLouis Pouchou, "X–Ray microanalysis of stratified specimens", Elsevier Science Publishers B. V., Analytica Chimica Acta. 283 (1993) pp. 81–97.

Schiebl et al., "A characteristic fluorescence correction factor for use in electron probe microanalysis", Microsc. Microanal, Microstruct. 2, 1991, pp. 413–423.

S. Sevov et al., "A comparison of recently developed correction procedures for electron probe microanalysis", Scanning, 1989, vol. 11, pp. 123–134.

August et al., "A method for determining the mass thickness of thin films using electron probe microanalysis", Scanning, 1987, vol. 9, pp. 145–155.

August et al., "Energy distribution of electrons transmitted through thin foils", Institut fur Angewandte aund Technische Physik, Technische Universitat Wien Wiedner Hauptstr.8–10, A–1040 Wien (Vienna), Austria.

Pfeiffer et al., "Models and their implementation", CEC–Vienna Reports, No. 92–08, Dec. 1992.

"MuFilm Data Collection & K–Ratio Measurement Documentation", pp. 2–10.

August et al., "Calculation and Comparison of the Surface Ionization", Institut fur Angewandte und Technische Physik, Technische Universitat Wien, Wiedner Hauptstr. 8–10, A–1040 Wien (Vienna), Austria.

August et al., "Calculation and Comparison of the Backscattering Factor R for Characteristic X–Ray Emission", Scanning, 1988, vol. 10, pp. 107–113.

August et al., "The Backscattering Factor as a Part of the Correction Procedures Employed in Quantitative Electron Probe Microanalysis", Radex–Rundschau, 1988, pp. 624–637.

August et al., "Calculation of the electron backscattering coefficient for thin films using a simple electron scattering model", J. Microsc. Spectrosc. Electron., 1989, vol. 14, pp. 189–201.

August, et al., "Theoretical prediction of the electron backscattering coefficient for multilayer structures", Journal of Microscopy, Feb. 1990, vol. 157, pp. 247–254.

* cited by examiner

FILM THICKNESS MEASUREMENT USING ELECTRON-BEAM INDUCED X-RAY MICROANALYSIS

CROSS-REFERENCE TO RELATED APPLICATION

This application claims priority of U.S. provisional patent application No. 60/210,337, filed Jun. 7, 2000, entitled "FILM THICKNESS MEASUREMENT USING ELECTRON-BEAM INDUCED X-RAY MICROANALYSIS," which is hereby incorporated by reference.

FIELD OF THE INVENTION

The present invention relates generally to X-ray microanalysis, and more specifically, to the application of X-ray analysis to measure film stack characteristics on semiconductor devices.

BACKGROUND

Generally, the industry of semiconductor manufacturing involves highly complex techniques for integrating circuits into semiconductor materials. Due to the large scale of circuit integration and the decreasing size of semiconductor devices, the semiconductor manufacturing process is prone to processing defects. Testing procedures are therefore critical to maintain quality control. Since the testing procedures are an integral and significant part of the manufacturing process, the semiconductor industry constantly seeks more accurate and efficient testing procedures.

A critical aspect of semiconductor fabrication involves the formation of the multiple conductive layers and liner layers. Each conductive layer includes the metal traces which form the paths along which electronic signals travel within semiconductor devices. Each of the conductive layers, are separated by a dielectric material layer and a liner layer. The dielectric material layer, commonly silicon dioxide, provides electrical insulation between the conductive layers. Portions of each conductive layer are connected to portions of other conductive layers by electrical pathways called "plugs." The liner layers are formed between each conductive layer and each dielectric material layer to prevent the conductive material from diffusing into the dielectric material layer. The liner layer inhibits a conductive layer from diffusing into an underlying dielectric and short circuiting with an adjacent conductive layer. Of course, such short circuit formations are likely to be detrimental to semiconductor performance. In particular note, copper, a common conductive material used in semiconductor devices, diffuses very aggressively into silicon dioxide. The thickness and composition of the conductive and liner layers must be formed under extremely small margins of error. Thus, systems capable of testing the characteristics of these layers are very important.

Some of the current methods for measuring film stack characteristics include a four-point probe test system, eddy current testing, X-ray fluorescence testing, photo-induced surface acoustic wave testing, and X-ray micrography techniques using a single energy dispersive detector (EDS) and/or a single wave length dispersive detector (WDS).

Unfortunately, each of these methods have associated disadvantages which limit their usefulness. For example, the four-point probe test system requires the destruction of the specimens. The eddy current test has difficulty resolving film stack thickness and also has a spot size which is relatively large as compared to areas of interest on a semiconductor device. X-ray fluorescence testing is also limited by a large spot size. X-ray fluorescence also has difficulty distinguishing different film stacks thickness, generally results in poor measurements, and is a time consuming process. It is important for the testing speeds to keep pace with the increasing fabrication speeds so that the goals of maximizing manufacturing throughput may be achieved. A specific problem with photo-induced surface acoustic wave methods is that it has difficulty resolving the thickness of copper layers; copper being a common conductor used in semiconductors. In addition to their specific problems, the above mentioned methods generally cannot accurately measure characteristics of a film stack which has multiple layers.

An EDS system is described in U.S. Pat. No. 4,675,889 by Wood et al., which is incorporated herein in its entirety. EDS systems are typically capable of collecting and counting X-ray photons for specific wide ranges of energy. Specific materials will be expected to have specific peak photon counts at specific energy levels. Although an EDS system may be adequate for measuring a single thin film, this system does not work well for measuring multiple films (e.g., such as a conductive layer and an underlying liner layer). Since EDS systems have relatively low associated signal to noise ratios, some or all of the peaks are not measured accurately or not detected at all. For example, when the number of X-ray photons for a particular material type are expected to peak at two energy levels that differ from each other by a relatively small amount, the two peaks are likely to be collected together within an energy range that includes both peak energy levels. Additionally, if one of the peaks is significantly smaller than the other peak, only the larger peak will be detected. A system utilizing a single WDS detector detects X-ray photons having a specific energy level. A drawback to the single WDS system is that the single WDS detector must be reconfigured each time it is desired to detect X-ray photons having a different energy level. This slows the testing process for a film stack of an integrated circuit since the WDS must be reconfigured for each sample type, and if desired, for each of the various characteristic emission levels for each sample.

Currently there is no satisfactory method capable of testing a pattern semiconductor wafer in a non-destructive manner, with a high degree of accuracy, having a high throughput, and with a relatively small spot size. In order for the semiconductor fabrication industry to achieve higher goals of manufacturing throughput, a system capable of testing film stacks having the above listed traits would be desirable.

SUMMARY

Accordingly, the present invention provides a non-destructive semiconductor testing system capable of efficiently measuring the composition and/or thickness of one or more layers within a film stack with a high degree of accuracy. In general terms, the present invention includes mechanisms for inducing X-ray emissions from a sample under test. The sample under test may have multiple film layers, such as conductor, insulator, and liner layers. In a specific embodiment, a charged particle beam is used to induce X-rays to emanate from one or more films on a semiconductor device. The charged particle beam penetrates at least two film layers (e.g., one conductive layer and one liner layer) of the film stack so that X-rays are produced in these penetrated layers. At least a portion of the X-rays are detected using one or more X-ray detectors that each detect X-ray photons having one or more specific energy levels.

The X-rays may then be analyzed to determine characteristics of the penetrated layers, such as composition and thickness.

In one embodiment, an apparatus for measuring film stack characteristics on an integrated circuit is disclosed. The apparatus includes an electron beam generator that is configurable to direct an electron beam towards the integrated circuit such that the electron beam penetrates at least a conductive film layer and a liner film layer of the integrated circuit. The electron beam thereby cause X-rays to emanate from the integrated circuit. The apparatus further includes X-ray detectors positioned above the integrated circuit so as to detect at least a portion of the X-rays emanating from the integrated circuit. Preferably, each of the multiple X-ray detectors are wavelength dispersive system (WDS) detectors. This embodiment appears to have a relatively high degree of accuracy (ie., 0.5%).

In another aspect, the invention pertains to a method for measuring film stack characteristics on a semiconductor device. An electron beam is directed towards the semiconductor device so that the electron beam penetrates at least a conductive film layer and a liner layer. At least a portion of the X-rays which are caused to emanate from the device are detected with multiple X-ray detectors which detect X-ray photons having a specific energy level. In a preferred embodiment, each of the multiple X-ray detectors are WDS detectors. A reflective surface within each WDS is positioned to focus X-rays of a predetermined energy level upon a sensor within each WDS. In other words, each WDS is configured to detect X-rays at a specific energy level. In yet another aspect, data obtained from the detected X-rays is collected and analyzed. The present invention also provides a computer-readable medium containing computer code for performing the above described method.

In alternative method and in computer-readable medium embodiments, at least one property of a film stack is determined using raw data (e.g., measured X-ray counts) associated with the film stack. A set of film stack characteristic values (e.g, thickness and/or compositions of a conductive and liner layer) are selected and used to generate predicted data (e.g., predicted X-ray counts at one or more specific energy levels) by solving equations which model the film stack. A new set of film stack characteristic values are selected when the difference between the predicted data and the raw data is larger than a certain margin of error. When the difference between the predicted data and the raw data is less than the margin of error, the selected characteristic values are believed to be a sufficiently accurate measurement of the actual characteristic values. In a specific embodiment, the raw and predicted data represent count values of X-rays at specific energy levels, and the film stack characteristic values represent a thickness and a composition value of the film layers in the film stack.

These and other features and advantages of the present invention will be presented in more detail in the following specification of the invention and the accompanying figures which illustrate by way of example the principles of the invention.

BRIEF DESCRIPTION OF THE DRAWINGS

The invention, together with further advantages thereof, may best be understood by reference to the following description taken in conjunction with the accompanying drawings in which:

FIG. 2B illustrates an electron in the L electron shell of the atom of the specimen of FIG. 2A filling the vacancy created in the K electron shell, and the simultaneous emission of the secondary X-ray photon.

DETAILED DESCRIPTION OF THE INVENTION

The present invention will be described in detail with reference to a few specific embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order to not unnecessarily obscure the present invention.

In general terms, X-ray micrography includes analysis of the X-ray region of the electromagnetic spectrum that is associated with a sample so as to gain information regarding the sample. The X-ray region of the electromagnetic spectrum includes frequencies that range from $1.0 \times 10^{17}$ Hz to $1.0 \times 10^{21}$ Hz. X-ray micrography is performed by bombarding a specimen with electrically charged particles which have sufficient energy to cause X-ray photons to be emitted from the specimen. By counting the emitted photons at one or more energy levels, the composition and thickness of conductive layers in a semiconductor device may be determined. The composition of a material may be determined since the specific energy levels of X-ray photons emitted from such material are related to the material's composition. For example, the thickness of a conductive layer may be determined by taking the integral of the number of X-ray photons around the characteristic energy emission levels. The integral taken is directly proportional to the thickness of the conductive layer. The actual thickness of a metal layer is then determined by applying a calibration factor, which is specific to each type of material being measured, to the count data. Procedures for determining composition and thickness of layers within a film stack are described further below with reference to FIGS. 7 through 10.

Figure 1:
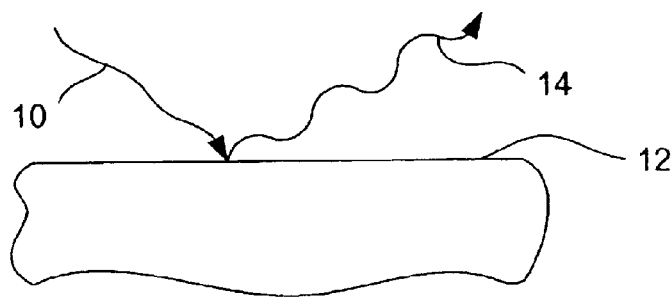
FIG. 1 illustrates an X-ray photon incident upon a specimen, and a resulting X-ray photon being emitted by the specimen material.
Figure 2A:
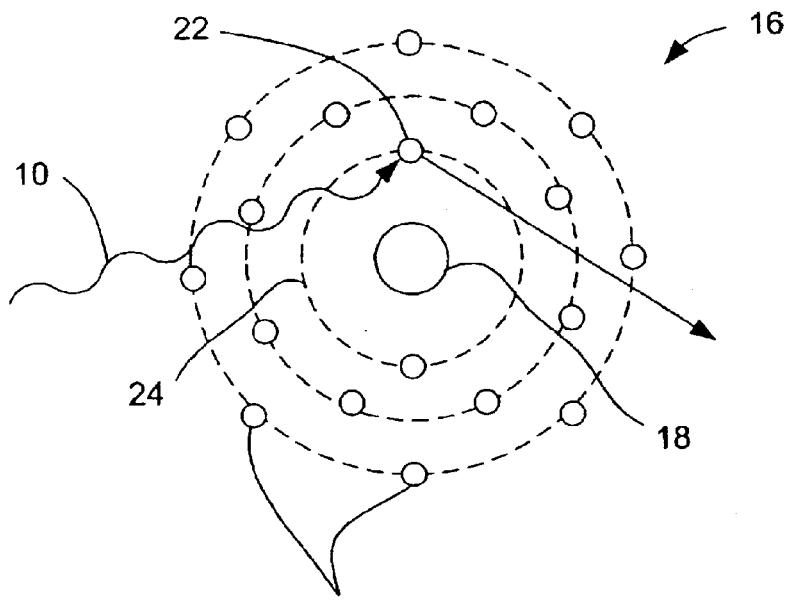
FIG. 2A illustrates the incident X-ray photon of FIG. 1 impacting an atom of the specimen, and the resulting ejection of an electron the innermost K electron shell of the atom.
Figure 2A:
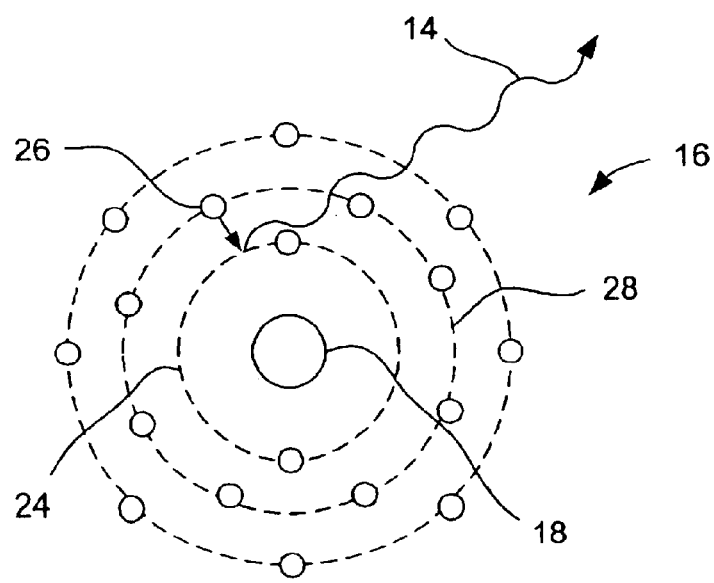

FIGS. 1, 2A, and 2B illustrate generally how X-ray photons may be caused to emanate from a specimen in accordance with one implementation of the present invention. FIG. 1 illustrates a charged particle 10, such as an electron, colliding with the surface of a specimen 12. The charged particle may collide with an atom of the specimen 12 and thereby causes an X-ray photon 14 to be emitted from the specimen 12. FIGS. 2A and 2B illustrate this collision event at the atomic level. FIG. 2A shows an atom 16 of the specimen 12. The atom 16 has a nucleus 18 surrounded by electrons 20 at different discrete distances from nucleus 18 called electron shells. A given electron shell has a binding energy level equal to the amount of energy required to remove an electron from the electron shell. The binding energy level of an electron shell is inversely proportional to the distance of the electron shell from the nucleus. The innermost electron shell of an atom is called the K shell, and has the highest binding energy associated with it. In FIG. 2A, K-shell electron 22 is located in K shell 24. The two shells beyond the K shell are the L and M shell, the M shell being the farthest away from the nucleus 18.

FIG. 2A also shows the charged particle 10 impacting atom 16 within the specimen 12. If the energy level of the particle 10 is greater than the binding energy level of a K-shell 24, the entire energy of the particle 10 is absorbed by atom 16 and one of the electrons in K shell 24 is ejected from the atom 16. As depicted in FIG. 2A, K-shell electron 22 is ejected from atom 16 after particle 10 is absorbed by atom 16.

With a vacancy in K shell 24, atom 16 is energetic and unstable. The most probable stabilization mechanism is the filling of the vacancy in K shell 24 by an electron located in an electron shell with a lower binding energy level. As shown in FIG. 2B, an L-shell electron 26 in L shell 28, which is farther from nucleus 18 than K shell 24, may fill the vacancy in K shell 24. As L-shell electron 26 fills the vacancy in K shell 24, atom 16 may simultaneously emit an X-ray photon 14 with energy $(N_K-N_L)$, where $N_K$ and $N_L$ are the binding energy levels of K and L shell, respectively. With a vacancy now in L shell 28, ionized atom 16 is more stable and less energetic.

The above described X-ray emission theory may be utilized to determine the composition and thickness of films within a film stack since X-ray emissions from the film stack depend on the film stack's composition and thickness values. That is, each material type has an associated atomic shell arrangement. Additionally, the binding energy level for each shell varies with material type. For example, a first material type emits X-rays at energy levels that differ from energy levels of a second material type. In other words, each material type has associated X-ray energy peaks at which X-rays are expected to be emitted. Thus, an unknown material's composition may be determined by comparing the unknown material's X-ray energy peaks with a known material's energy peaks. When a match is found, the unknown material is identified as having the same composition as the matching material.

Figure 3:
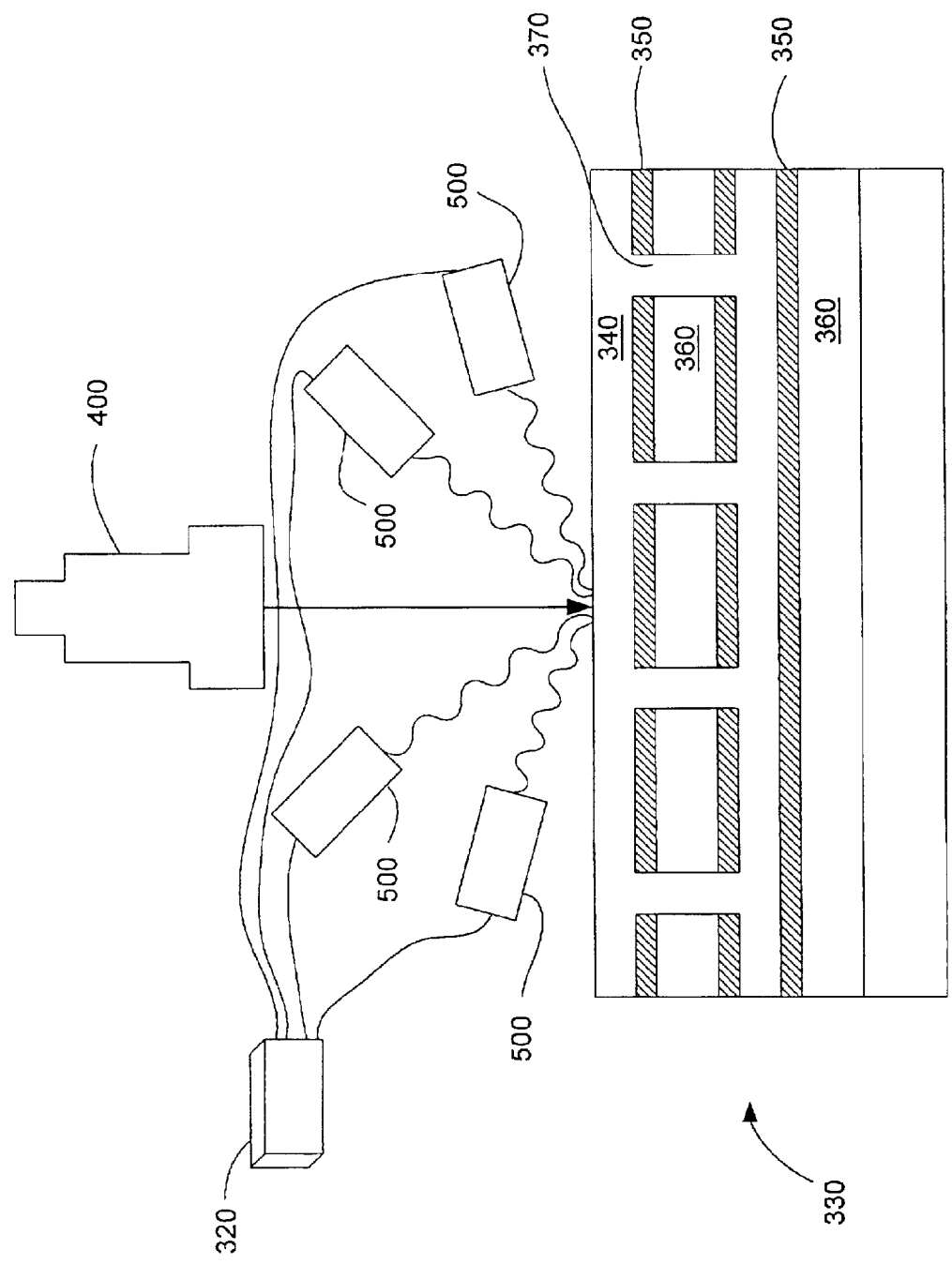
FIG. 3 illustrates an electron beam induced X-ray microanalysis test system according to one embodiment of the present invention.

FIG. 3 illustrates a system utilizing an electron beam induced X-ray microanalysis test system according to one embodiment of the present invention. The system represented in FIG. 3 includes a beam generator 400, which directs a charged particle beam at the specimen 330. The typical spot size of the system is approximately 10 microns in diameter. However, the spot size may range between 1–100 microns in diameter. The specimen 330 is a multi-layered semiconductor wafer for which layer thickness and composition measurements are desired. X-ray detectors 500 are positioned above the specimen 330 in order to collect the X-ray photons emitted from the specimen 330. Each of the X-ray detectors are coupled with an analysis unit 320. The analysis unit 320 can be configured to analyze the data collected by the X-ray detectors 500 and to generate useful information concerning the individual layers. The analysis unit 320 may take the form of any suitable processing or computing system, such as a workstation.

Figure 4:
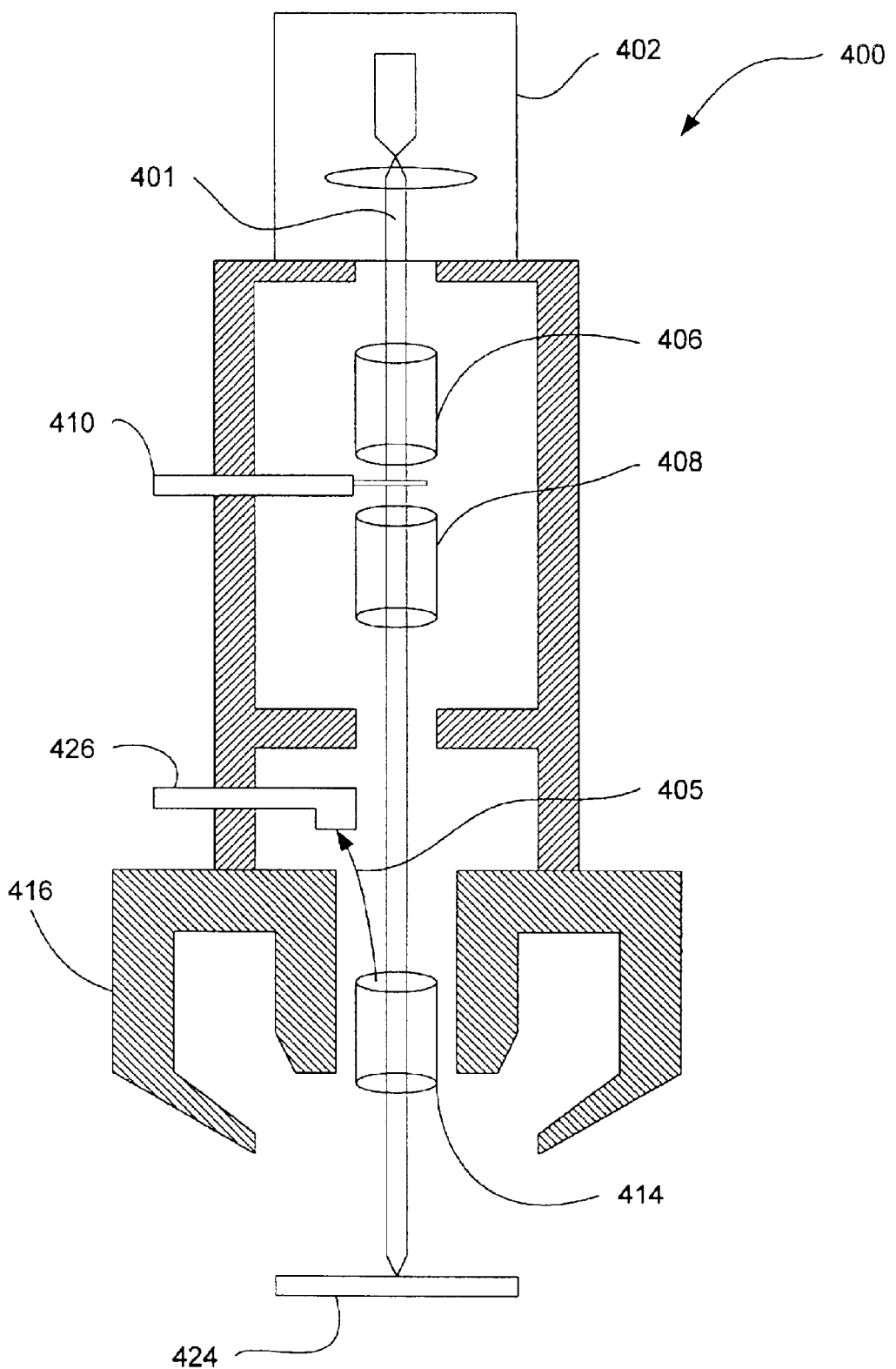
FIG. 4 illustrates a typical scanning electron microscope in accordance with one embodiment of the present invention.

The beam generator 400 may be any suitable device that directs charged particles towards a specimen, and which, in turn, causes X-rays to emanate from the sample under test. The generator 400 is capable of projecting the charged particles with sufficient energy to penetrate at least two layers of the film stack on a integrated circuit. By way of example, a conductive layer and a liner layer may be two of the film stack layers penetrated by the beam generator 400. Preferably, the particles penetrate substantially through the entire conductive and liner layers so as to cause X-rays to emanate from the entire width of the respective layers. As a result, X-ray measurements from the entire thickness of the penetrated layers may then be taken. By way of example, the beam generator 400 may take the form of a scanning electron microscope (SEM). FIG. 4 is a diagrammatic representation of a typical scanning electron microscope (SEM) system 400. As shown, the SEM system 400 includes an electron beam generator (402 through 416) that generates and directs an electron beam 401 substantially toward an area of interest on a specimen 424. The SEM system 400 also includes a detector 426 arranged to detect charged particles 405 (secondary electrons and/or backscattered electrons) emitted from the specimen 424.

As shown, the electron beam generator includes an electron source unit 402, an alignment octupole 406, an electrostatic predeflector 408, a variable aperture 410, a wien filter 414, and a magnetic objective lens 416. The source unit 402 may be implemented in any suitable form for generating and emitting electrons. For example, the source unit 402 may be in the form of a filament that is heated such that electrons within the filament are excited and emitted from the filament. The octupole 406 is configured to align the beam after a particular gun lens voltage is selected. In other words, the beam may have to be moved such that it is realigned with respect to the aperture 410.

The aperture 410 forms a hole through which the beam is directed. The lower quadrupole 408 may be included to compensate for mechanical alignment discrepancies. That is, the lower quadrupole 408 is used to adjust the alignment of the beam with respect to any misaligned through-holes of the SEM through which the beam must travel. The magnetic objective lens 416 provides a mechanism for accelerating the beam towards the sample. Finally, the Wien filter 414 deflects secondary electrons towards the detector 426.

The specimen or sample 330 may take a variety of forms for which certain measurements are desired. Specifically, the electron beam induced X-ray microanalysis test system may be used to measure the film characteristics of various thin film devices such as a semiconductor wafer or a magnetic recording head. In the illustrated embodiment, the specimen 330 is a semiconductor wafer which contains alternating conductive 340, dielectric 360, and liner 350 layers formed on a substrate of semiconductor material. The wafer 330 includes multiple conductive layers 340 which couple devices (e.g., transistors and capacitors) within a semiconductor device. Portions of each conductive layer 340 are typically coupled to an adjacent conductive layer portion 340 through a connection path called a "plug" 370. Typically, the conductive layer is typically about 10,000 Angstroms in thickness. Each conductive layer 340 is also separated by a dielectric material layer 360. The dielectric material, for example silicon dioxide, electrically insulates each conductive layer 340 to prevent unwanted short circuits. At the beginning of the fabrication process, the conductive layers have initial thicknesses of 1000 Angstroms. During the fabrication process, additional materials are added to form the conductive layers and therefore result in conductive layers having thickness of approximately 10,000 Angstroms. In some implementations of the test system, the initial and final thicknesses of the conductive layers will be measured.

Since conductors, such as Cu, may easily diffuse into the adjacent dielectric layers 360, a thin liner layer 350 is formed between the conductive layers 340 and the dielectric layers 360. The liner layers 350 prevent each conductive layer 340 from diffusing into the dielectric layer and shorting with an adjacent conductive layer. Such a short may be detrimental to the proper operation of the semiconductor device. Any suitable liner layer material may be utilized to prevent a conductive layer from diffusing into an adjacent conductive layer. For example, a liner layer of Tantalum or Tantalum-Nitride may be used. The liner layer may have any suitable thickness, such as 300 Angstroms. The formation of the conductive and liner layers are monitored closely since they affect semiconductor device operation. The microanalysis system of the present invention is advantageously capable of measuring at least one conductive layer 340 and at least one liner layer 350 of a semiconductor wafer.

Figure 5:
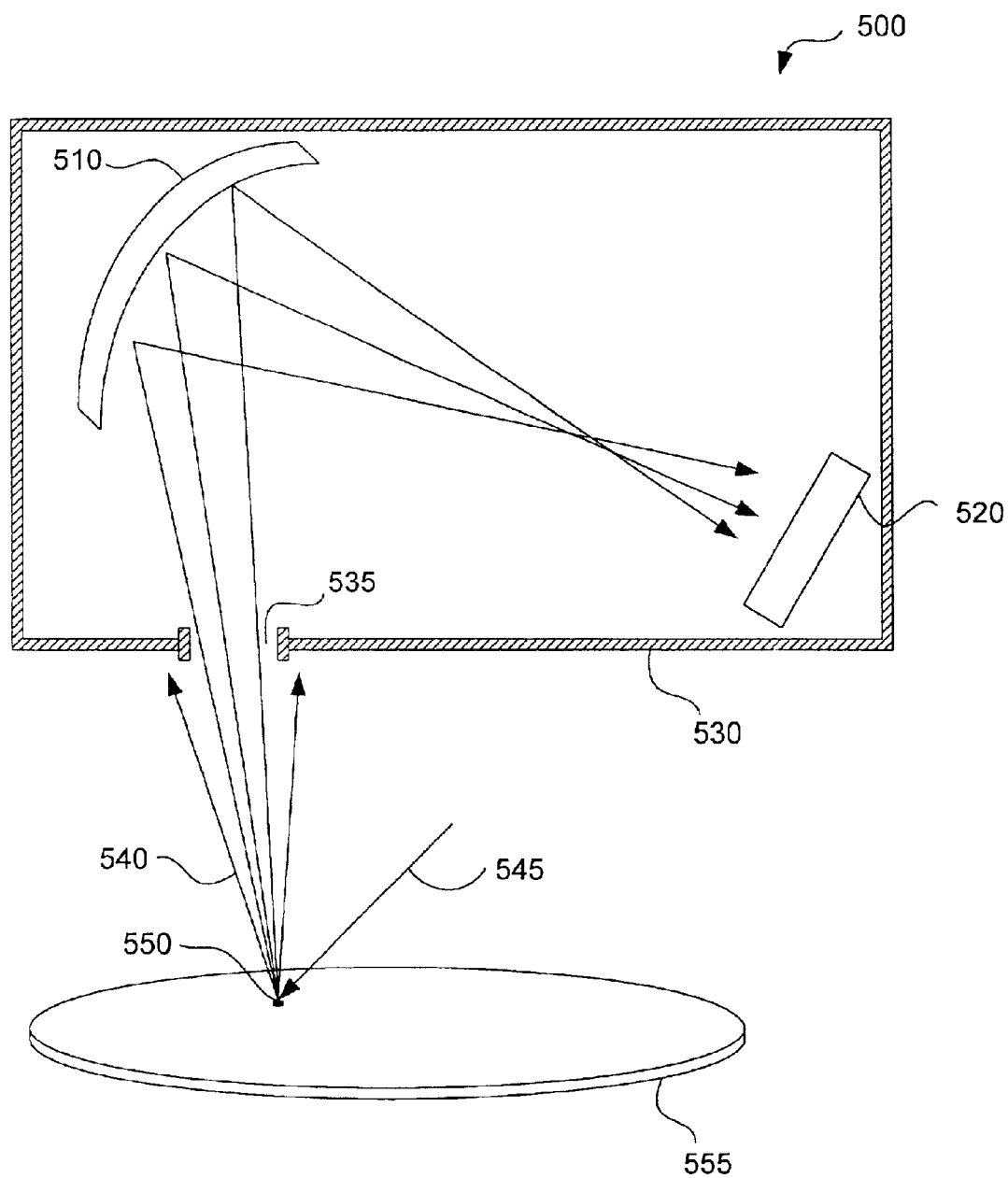
FIG. 5 illustrates a cross-sectional view of a wavelength dispersive system (WDS) X-ray detector of FIG. 3 in accordance with one embodiment of the present invention.

Any suitable detector for measuring X-rays at specific energy levels may be utilized. FIG. 5 illustrates a cross-sectional view of a wavelength dispersive system (WDS) X-ray detector in accordance with one embodiment of the present invention. Each X-ray detector 500 includes a housing 530 having an aperture 535. Although preferred, the housing and aperture are optional and are not required for practicing the techniques of the present invention. An electron beam 545 is directed to a focus point 550 on a thin film device 555 (i.e., a semiconductor wafer). The electron beam 545 causes photons 540 to emanate from the focus point 550. The aperture 535 permits a limited amount of photons 540 to enter each detector 500. Upon entering the detector 500, each photon travels along a path to a concave reflective surface 510. The reflective surface 510 directs a portion of photons to a sensor 520. The reflective surface 510 is designed and positioned so that only photons with a specific energy level are directed to the sensor 520. The reflective surface 510 may be positioned to direct only photons with an energy level characteristic of a certain material to facilitate a film characterization process. By detecting photons of only a specific energy level, detector 500 is capable of obtaining high signal to noise ratios. It should be noted that the reflective surface may be a Bragg reflector or a crystal capable of directing photons towards the sensor.

Figure 6:
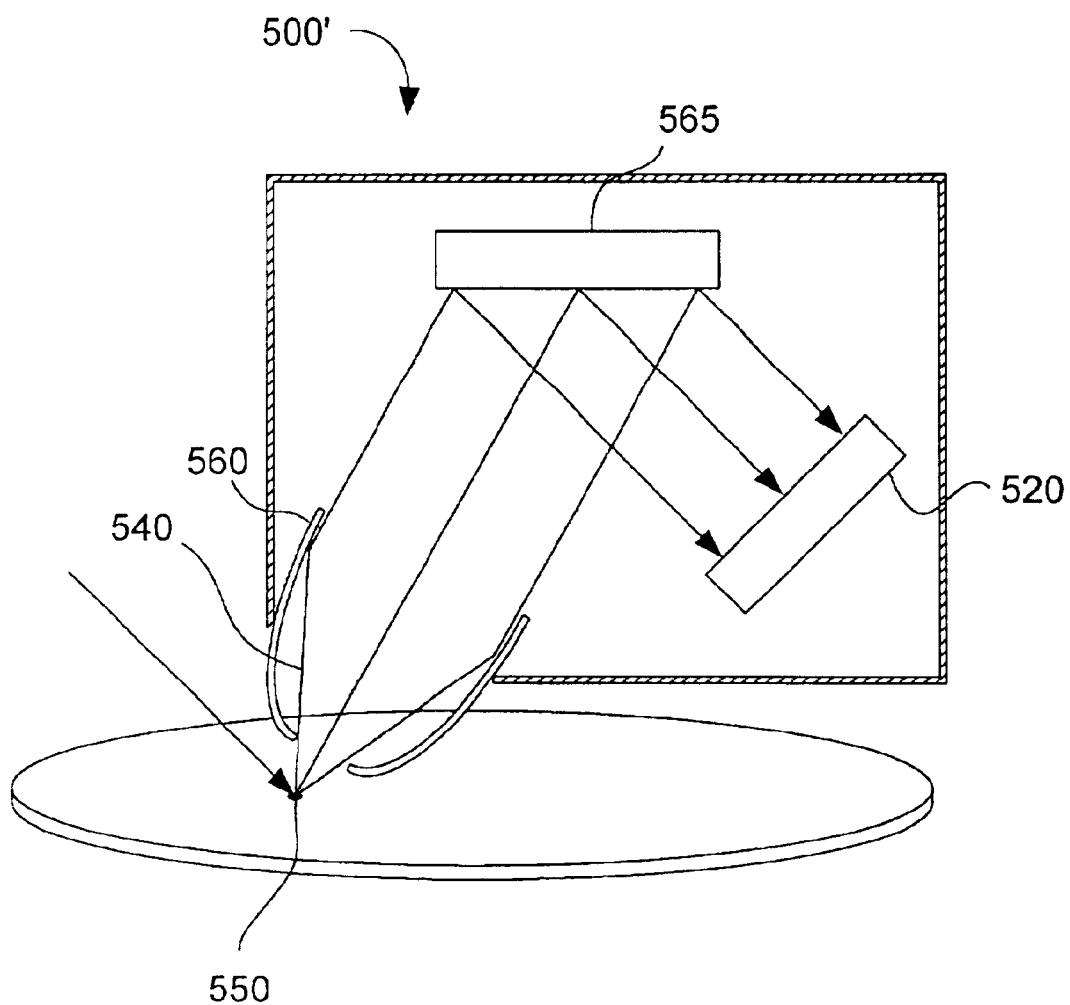
FIG. 6 illustrates a cross-sectional view of an alternative and preferred embodiment of the WDS X-ray detector.

A cross-sectional view of an alternative and preferred embodiment of a WDS X-ray detector 500' is illustrated in FIG. 6. Detector 500' has a collimator 560 that captures the photons 540 emanating from the focus point 550, and then through its reflective surfaces causes the photons 540 to travel in substantially parallel paths. The collimator 560 is generally made from metal foil material. The photons then reflect off of a substantially flat reflective surface 565 such that the photons 540 continue in parallel paths towards the sensor 520. Similarly with detector 500, the reflective surface 565 in detector 500' may also be Bragg reflector or a crystal.

A common device which contains the general elements of the detector 500 and 500' is a Wavelength Dispersive System (WDS). By utilizing multiple WDS detectors, one or more photon peaks may be detected for each type of material that is expected to be present within the measured film stack of the specimen. That is, characteristic emission levels for one or more types of material in the film stack may be measured. One or more individual detectors may also be dedicated to detect the various characteristic emission levels for each type of material. For example, two WDS detectors may be dedicated for detecting two peaks associated with a copper material. As described earlier each material has emission levels characteristic of photons released due to an electron falling from each of the K, L, or M shells. By using multiple WDS detectors, the test system is able to obtain information for each of a multiple number of film layers.

Another type of detector, an Energy Dispersive System (EDS), collects photons in a wide spectrum of energies. EDS are capable of collecting a greater range of signals. As a result however, EDS detectors also collect photons having energies surrounding the characteristic photon energies. This causes EDS detectors to have lower signal to noise ratios.

The test system of the illustrated embodiment is capable of obtaining measurements having precision within 0.5% accuracy. Film stack thickness measurements may also be made within two seconds if the electron beam current is increased to approximately $1.0 \times 10^{-5}$ Amps. Thus, this test system allows for both accurate testing at a high throughput rate.

Figure 7:
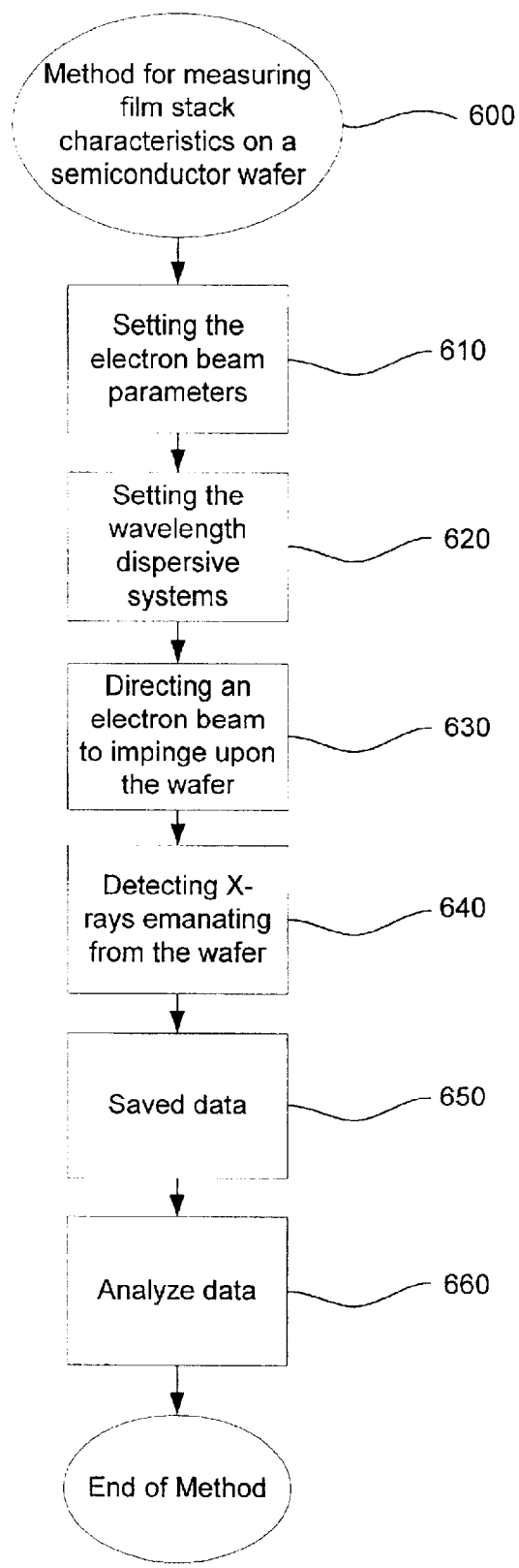
FIG. 7 shows a flow diagram representing a procedure for measuring film stack characteristics on a semiconductor wafer in accordance with one embodiment of the present invention.
Figure 8A:
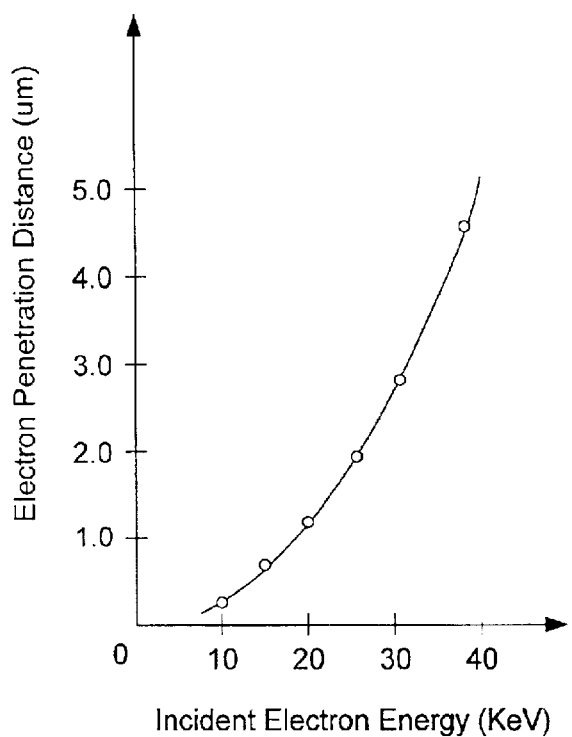
FIG. 8A illustrates a graph representing the depths to which an electron beam will penetrate depending upon the electron beam energy level.
Figure 8B:
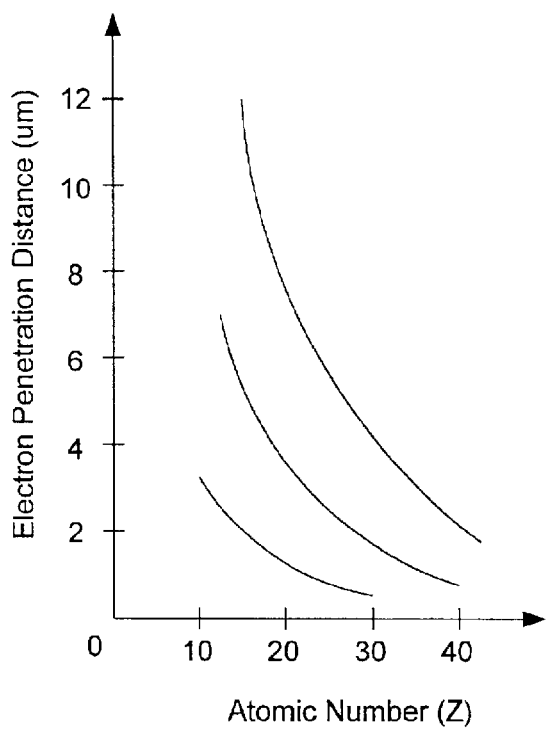
FIG. 8B illustrates a graph representing how the electron beam penetration depth varies with an element's atomic number while at a constant energy level.

FIG. 7 illustrates a flow diagram representing one particular implementation of a method for measuring film stack characteristics on a semiconductor wafer. Initially, electron beam 400 parameters are set in operation 610. Parameters such as the electron beam current and voltage are set so that the electron beam has a landing energy sufficient for the beam to penetrate at least one conductive layer and one liner layer. Landing energy is defined as the energy at which the beam hits the specimen. In addition to the beam current and voltage, the scan pattern of the electron beam may affect the charge distribution of on the specimen 330, and thus, affect how the information is collected during the testing procedure. Charts, such as the ones illustrated in FIGS. 8A and 8B, may be used to determine the energy levels at which to set the electron beam 400 so that the desired layers are penetrated by the electron beam. These charts are well known and widely available to those skilled in the art. FIG. 8A shows the depths to which an electron beam will penetrate as the electron beam energy level varies. FIG. 8B shows how the electron beam penetration depth varies with an element's atomic number while at a constant electron beam energy level. Typical electron beam energy levels range from 15 to 30 keV.

After the beam parameters are set for the specific specimen, each of the WDS X-ray detectors 500 are set to detect the photons which will emanate from the layers within the specimen in operation 620. That is, the detectors 500 are set to detect photons having specific X-ray energy levels. Ideally, one WDS 500 is set to detect photons having energy levels corresponding to the characteristic X-ray energy emission levels of each material in the film stack to be analyzed. Multiple detectors 500 may also be set to detect X-ray energies of a single material in order to detect each of the multiple characteristic emission levels of that specific material. Each emission level for a single material represents photons emitted as a result of an electron falling from a different electron shell (i.e., K, L, M, etc.). A WDS is set for a specific emission level by orienting a reflective surface 510 at a specific angle such that only X-ray photons centered around the desired energy level are directed at a sensor 520. The sensor 520 will then be able to collect photons for analysis purposes. The information collected by the detectors may be transmitted to processing system 320 which is connected to each detector 500. Processing system 320 will then perform the desired analysis.

Figure 9:
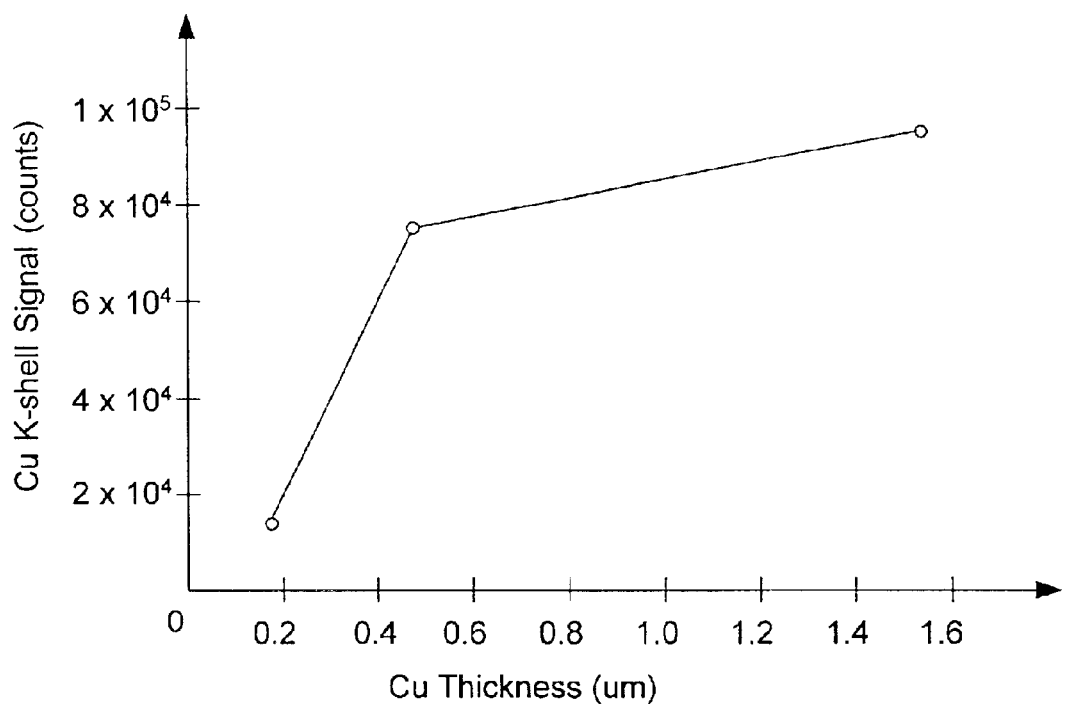
FIG. 9 illustrates a graph representing the counts detected for the K shell emission levels for a copper layer as the thickness of a copper layer increases.
Figure 10:
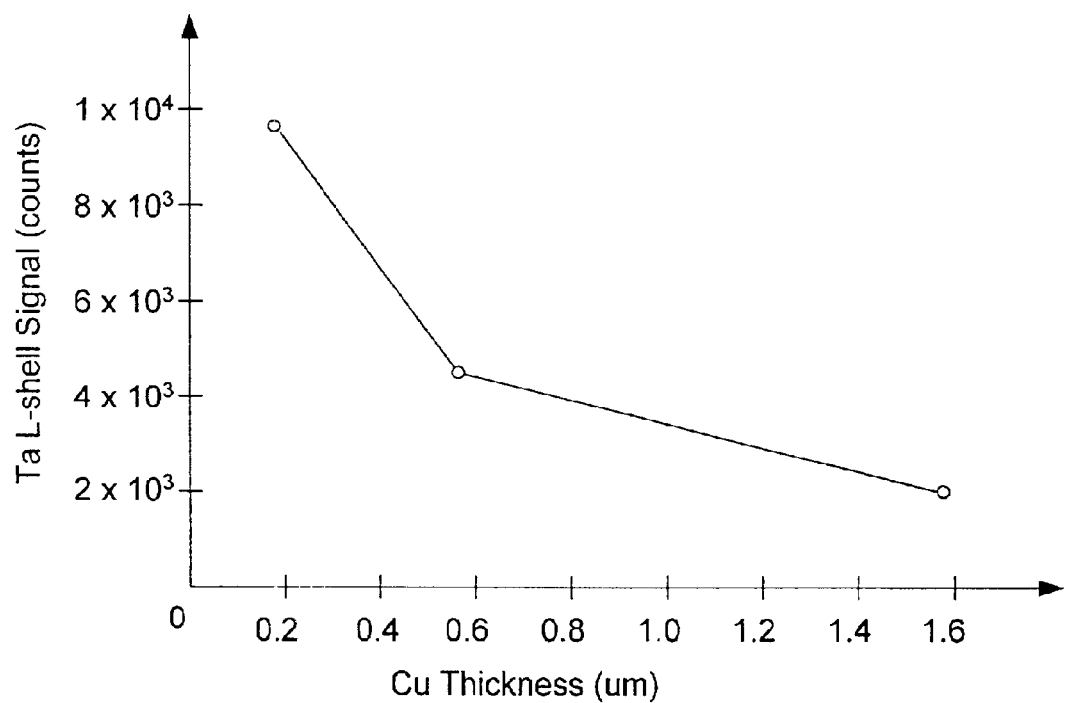
FIG. 10 illustrates a graph representing the counts detected for the K shell emission levels for a Tantalum layer as the thickness of a copper layer, formed above the Tantalum layer, increases.

After the electron beam 400 and the X-ray detectors 500 are properly set, the electron beam probe 400 is activated so that an electron beam impinges upon the semiconductor wafer 330 in operation 630. The electron beam penetrates at least one conductive layer and one liner layer, thereby, causing X-ray photons to emanate from the penetrated layers. X-ray photons emanating from each layer will be used to gain information about each of the respective layers. In operation 640, these X-rays are detected by the X-ray detectors 500. The number of X-rays at each characteristic emission energy level are counted. The number of X-rays counted is designated as the count for that particular emission level. FIGS. 9 and 10 show illustrative charts of the counts for the emission levels for a copper (Cu) K-shell emission and a tantalum (Ta) layer L-shell emission, respectively, wherein the Cu layer is formed on top of the Ta layer. The counts for each layer are illustrated for varying thickness values of the Cu layer. In FIG. 9, it can be seen that as the thickness of the Cu layer increases, so to does the count. In contrast, in FIG. 10, the count for Ta decreases as the thickness of the Cu layer increases since fewer X-ray photons are created as the Cu layer increases. Fewer X-ray photons for the Ta layer are created as the Cu layer increases in thickness because the electron beam penetrates to the Ta layer to a lesser degree as the Cu layer increases in thickness.

Data from the collected X-rays is saved by the processing system 320 in operation 650. The data is then analyzed in operation 660. Any suitable analysis technique may be used for determining characteristics of the film stack based on X-ray emission at specific energy levels. For example, a regression routine may be used. The procedure for measuring film stack characteristics 600 is completed when the conductive layer characteristics are obtained through the regression routine. Alternative methods of analyzing the collected data may also be used. For example, a series of calibration measurements are made, then measurement points between the calibration points are obtained through interpolation techniques.

Figure 11:
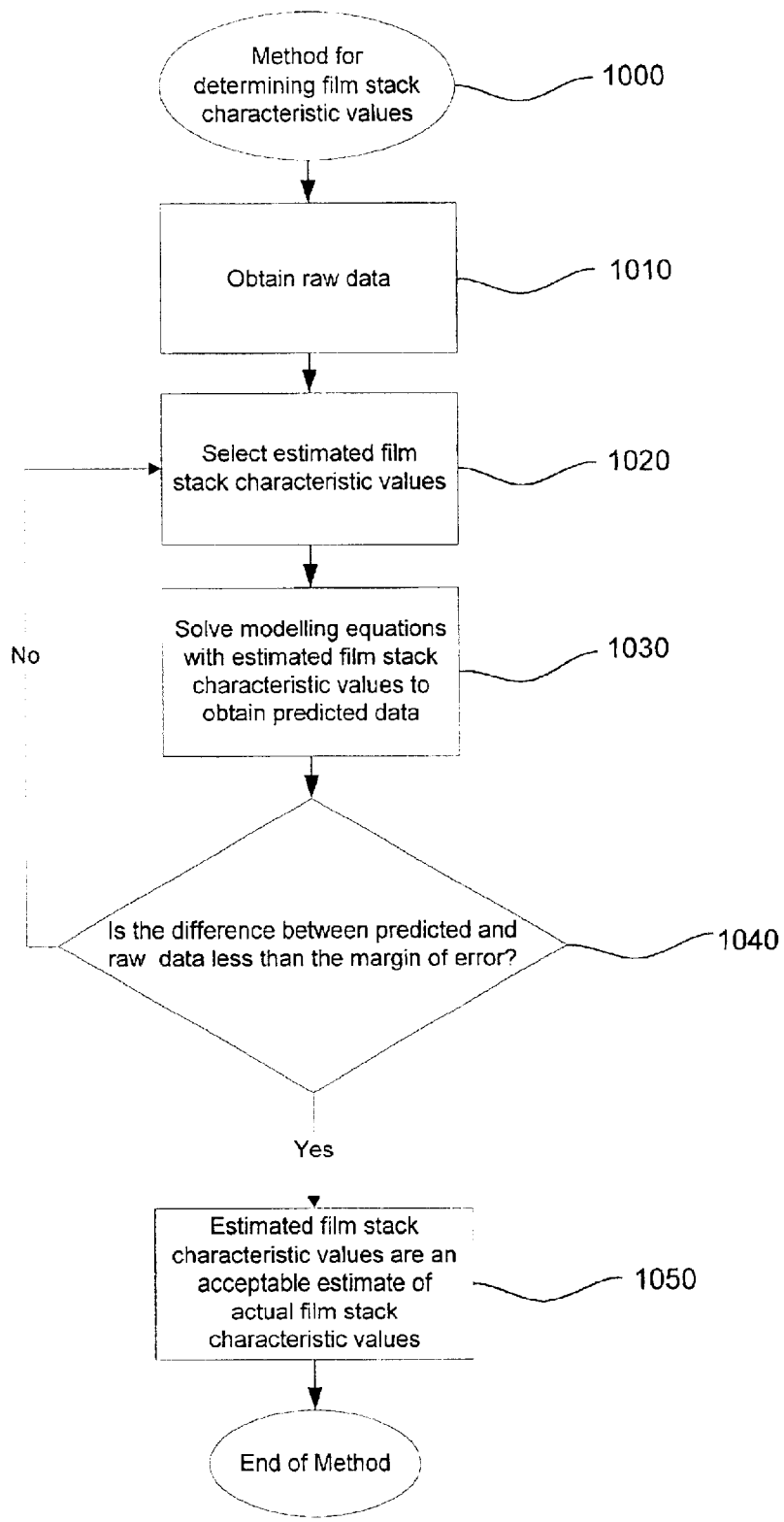
FIG. 11 illustrates a flow diagram representing a procedure for determining film stack characteristic values in accordance with one embodiment of the present invention.

FIG. 11 illustrates a flow diagram representing the procedure 1000 for determining particular film stack characteristic values. Generally, the procedure 1000 is a regressive technique where certain computational operations are repeated until a desired result is obtained. The operations include generating predicted data (the counts) regarding the film stack layers by inputting estimated film stack characteristics, such as thickness and composition values, into equations which model X-ray emission from the film stack layers. In other words, X-ray emission results are calculated for a film stack having the input estimated film stack characteristics. Various estimated film stack values are repeatedly inputted into the modeling equations until the resulting predicted data values closely match the data actually obtained from the X-ray micrography system.

Any suitable regression technique may be utilized to repeatedly generate x-ray emission predictions for a particular film stack model and match such predictions to the measured raw data. For example, the well known Monte Carlo regression technique may be utilized. Monte Carlo techniques are useful for solving computationally complex equations, such as the above described equations. Another example of a regression technique that may be used is the Phi-Rho-Z model. Several software applications are available that automatically model films stacks with the Phi-Rho-Z model. For example, the Stratagem, available from Samx Guyan Court, in France, or the Citzaf, available from NIST (National Institute of Standard and Technology), software packages may be used. Parameters that are relevant to x-ray emission are input into the software, along with the measured raw data. The software then repeatedly uses the model equations to produce predicted data until the predicted data matches the raw data. For this specific software application, the parameters include the raw data and starting estimated values for film compositions, film thickness, landing energy of the electron beam, beam current, take-off angle, and detector efficiency. When the predicted data values (e.g., output from the film stack model) closely match the raw data values, it is believed that the estimated film stack characteristics are a good estimate of the actual film stack characteristics. The accuracy of this method, is of course, limited by the ability of the modeling equations to accurately predict the characteristics of the actual specimen.

As shown in FIG. 11, raw data is initially obtained from the X-ray micrography system, for example, in operation 1010. In operation 1020, a first set of estimated film stack characteristics values are selected to be inputted into the modeling equations. In operation 1030, the equations are solved according to the estimated characteristic values in order to generate a set of predicted data values. In operation 1040, the raw data and the predicted data are compared. If the difference between the respective values is less than a certain margin of error, then the estimated film stack characteristic values are an acceptable estimate of the actual film stack characteristics. However, if the difference between the respective values are greater than the margin of error, then a new set of estimated film stack characteristics are selected. The regression operations (i.e., 1020, 1030 and 1040) continue until the difference in data values is less than the estimated margin of error, which is represented in operation 1050. A margin of error should be approximately equal to or less than 0.5% for acceptable estimates of film stack characteristics.

While this invention has been described in terms of several preferred embodiments, there are alteration, permutations, and equivalents which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

We claim:

1. An apparatus for measuring film stack characteristics of a sample, the apparatus comprising:

a beam generator configurable to direct an electron beam towards the sample such that the electron beam completely penetrates a plurality of desired layers of the film stack, the electron beam causing X-rays to emanate from the sample;

at least a first and a second wavelength dispersive X-ray detector positioned above the sample wherein each detector detects X-rays about a different characteristic emission level, wherein the first detector is configured to detect X-rays having characteristic emission levels for a top layer of the film stack and the second detector is configured to detect X-rays having characteristic emission levels for an underlying layer that lies beneath the top layer, whereby material characteristics of the desired layers can be measured simultaneously; and an analysis unit that collects data resulting from the detected X-rays, wherein the data that is collected is raw data, the analysis unit also configured to compare predicted data derived from one or more equations that model the film stack against the raw data.

2. The apparatus as recited in claim 1 wherein the first X-ray detector is configured to detect X-rays of a specific energy level.

3. The apparatus as recited in claim 1 wherein the wavelength dispersive system contains a reflective surface and a sensor, the reflective surface configured to direct X-rays of a predetermined energy level to the sensor.

4. The apparatus as recited in claim 1 further comprising a processor linked to the beam generator and to the first X-ray detector.

5. The apparatus as recited in claim 4 wherein the processor is configured to control the first X-ray detector so that it detects X-rays of a specific energy level.

6. The apparatus as recited in claim 4 wherein the processor is configured to control the beam generator so that the electron beam directed to the sample penetrates at least a conductive film layer and a liner film layer of the sample.

7. An apparatus as recited in claim 1 wherein each of the characteristic emission levels correspond to a different layer of the film stack.

8. An apparatus as recited in claim 1 wherein the electron beam completely penetrates the top and the underlying layers of the film stack so that the thickness of the top and the underlying layers can be determined.

9. An apparatus as recited in claim 1 wherein the electron beam completely penetrates at least a conductive film layer and a liner film layer of the sample.

10. An apparatus as recited in claim 1 wherein the electron beam is set at a substantially constant voltage level.

11. The method of determining film stack characteristic values as recited in claim 10 further comprising recording the set of estimated film stack characteristic values when a difference between the predicted data and the raw data is equal to or smaller than the predetermined margin of error, wherein the estimated film stack characteristic values are an acceptable estimate of the film stack's characteristic.

12. A method for measuring at least one characteristic of a film stack on a sample, the method comprising:

directing a charged particle beam towards the sample such that the charged particle beam completely penetrates at least two layers of the film stack, the charged particle beam causing X-rays to emanate from the sample;

detecting X-rays at a first characteristic emission level that represents an emission level for a top layer of the film stack using at least a first wavelength dispersive X-ray detector that is positioned above the sample;

detecting X-rays at a second characteristic emission level that represents an emission level for an underlying layer of the film stack using at least a second wavlength dispersive X-ray detector that is positioned above the sample, the underlying layer being a layer of material underneath the top layer;

collecting data resulting from the detected X-rays, wherein the data that is collected is raw data; and comparing predicted data derived from one or more equations that model the film stack against the raw data.

13. The method for measuring as recited in claim 12, further comprising configuring the first X-ray detector to detect X-rays of a specific energy level.

14. The method for measuring as recited in claim 12 further comprising positioning a reflective surface contained within the wavelength dispersive system in an orientation to direct X-rays of a predetermined energy level to a sensor contained within the wavelength dispersive system.

15. The method for measuring as recited in claim 12, the method further comprising selecting a charged particle beam energy and a charged particle beam current at which the charged particle beam will be produced.

16. The method for measuring as recited in claim 12 wherein a conductive film layer and a liner film layer are two of the at least two layers that are penetrated by the charged particle beam.

17. The method of determining film stack characteristic values as recited in claim 12 wherein the raw and predicted data represent a count value of X-rays having a specific energy level, the count value being the total number of X-rays received by each of the wavelength dispersive systems over a period of time.

18. A method as recited in claim 12 wherein each of the characteristic emission levels correspond to a different layer of the film stack.

19. A method as recited in claim 12 wherein the charged particle beam completely penetrates the thickness of the top and the underlying layers of the film stack so that the thickness of the top and the underlying layers are determined.

20. An apparatus for measuring the thickness of two or more layers within a film stack sample, the apparatus comprising:

a beam generator configurable to direct an electron beam towards the sample such that the electron beam completely penetrates at least two layers of the film stack, the electron beam causing X-rays to emanate from the sample;

at least a first and a second wavelength dispersive X-ray detector positioned above the sample wherein each detector is configured to detect a respective portion of the X-rays emanating from the sample, whereby material characteristics of the at least two layers can be measured simultaneously; and an analysis unit that collects data resulting from the detected X-rays, wherein the data that is collected is raw data, the analysis unit also configured to compare predicted data derived from one or more equations that model the film stack against the raw data.

21. An apparatus as recited in claim 20 wherein the first X-ray detector is configured to detect X-rays of a specific energy level.

22. An apparatus as recited in claim 20 wherein the first X-ray detector is a wavelength dispersive system.

23. An apparatus as recited in claim 22 wherein the wavelength dispersive system contains a reflective surface and a sensor, the reflective surface configured to direct X-rays of a predetermined energy level to the sensor.

24. An apparatus as recited in claim 20 further comprising a second X-ray detector, wherein the first and second X-ray detectors are wavelength dispersive systems.

25. A method for measuring as recited in claim 12, further comprising:
- selecting a set of estimated film stack characteristic values; and
- obtaining the predicted data by solving the one or more equations that model the film stack using the set of estimated film stack characteristic values.

26. A method for measuring as recited in claim 25, further comprising:
- selecting a new set of estimated film stack characteristic values when a difference between the predicted data and the raw data is larger than a predetermined margin of error; and
- obtaining a new set of predicted data by solving equations which model the film stack using the new set of estimated film stack characteristic values when the difference between the predicted data and the raw data is larger than the predetermined margin of error.

27. An apparatus as recited in claim 20 wherein the electron beam can be scanned over the film stack sample in a scan pattern.

28. An apparatus as recited in claim 27 further comprising:
- an octupole for aligning the electron beam generated by the beam generator; and
- a lower quadrupole for further adjusting the alignment of the electron beam.

* * * * *